United States Patent [19]
Pan et al.

[11] Patent Number: 5,085,850
[45] Date of Patent: Feb. 4, 1992

[54] ANTI-PLAQUE COMPOSITIONS COMPRISING A COMBINATION OF MORPHOLINOAMINO ALCOHOL AND METAL SALTS

[75] Inventors: Pauline H. Pan, Morris Plains; Steven S. Dills, Hackettstown; Donald M. Lynch, Flemington; Lori D. Kumar, Princeton, all of N.J.

[73] Assignee: Warner-Lambert Company, Morris Plains, N.J.

[21] Appl. No.: 612,037

[22] Filed: Nov. 9, 1990

[51] Int. Cl.$^5$ .............................................. A61K 7/16
[52] U.S. Cl. ...................................... 424/49; 424/48; 424/440; 514/901
[58] Field of Search .................. 424/54, 49, 404, 440, 424/48; 514/901, 902

[56] References Cited

U.S. PATENT DOCUMENTS

| | | | |
|---|---|---|---|
| 4,894,221 | 1/1990 | Hethestam et al. | 424/54 |
| 4,970,064 | 11/1990 | Adam et al. | 424/52 |

Primary Examiner—Thurman K. Page
Assistant Examiner—D. Colucci
Attorney, Agent, or Firm—Carl W. Battle

[57] ABSTRACT

Compositions having improved anti-plaque and anti-gingivitis activity comprise a synergistic combination of a) a morpholinoamino alcohol or salt thereof, such as 3-(4-propylheptyl)-4-(2-hydroxyethyl) morpholine, and b) a metal salt, such as the salts of divalent zinc, copper and magnesium.

11 Claims, No Drawings

ANTI-PLAQUE COMPOSITIONS COMPRISING A COMBINATION OF MORPHOLINOAMINO ALCOHOL AND METAL SALTS

BACKGROUND OF THE INVENTION

Bacterial aggregation on the teeth known as plaque has been identified as a cause of dental caries, gingivitis, periodontitis and other gum diseases. Mechanical methods have been used for sometime for the prevention of dental plaque but have not generally achieved sufficient results. Studies have shown that mechanical methods such as the use of dental floss and interspace brushes do not eliminate interproximal plaque. During the past decade or more chemical plaque control as a substitute or supplement to mechanical methods has been tried.

Octapinol has been tested for its ability to reduce plaque formation and the development of gingivitis by Willard, Edwardsson, Attstom and Matsson, "The effect of Octapinol on dento-gingival plaque and development of gingivitis", *Journal of Periodontal Research*, Volume 18, pages 429–437, (1983). Here it is reported that octapinol may prevent the development of plaque. Some adverse side effects of octapinol are its toxicity, lasting bitter taste and its brownish staining of the teeth.

U.S. Pat. No. 4,636,382 describes morpholino compounds which are useful for the inhibition or removal of dental plaque. The '382 patent also discloses that a wide variety of chemical and biological agents have been suggested for the inhibition of plaque, such as penicillin, chlorohexidine, 8-hydroxyquinoline and ethylenediamine tetraacetate. However, many of these chemical and biological agents are described as exhibiting insignificant effects and often causing serious side effects. The morpholino compounds of the '382 patent are described as having a low antibacterial effect and lacking undesirable side effects such as discoloration of the teeth.

U.S. Pat. No. 4,610,871 describes the use of monoalkyl or dialkyl ethers of dianhydrohexitols to inhibit the formation of plaque and calculus on teeth. U.S. Pat. No. 4,178,363 describes the use of n-undecylenic acid or a calcium or zinc salt thereof for reducing dental plaque and infections of the teeth and gums. U.S. Pat. N. 4,119,711 describes spiro 1-(hydroxyalkyl)-piperidino derivatives which have efficacy in reducing the formation of plaque. U.S. Pat. No. 3,976,765 describes bis-biguanido hexanes in combination with nonionic surfactants and certain foam stabilizers for use in a variety of oral preparations.

Additionally, U.S. Pat. No. 3,887,712 discloses that alexidine dihydrofluoride is useful in the treatment of dental plaque, calculus, gingivitis and related periodontal diseases. U.S. Pat. No. 4,160,821 discloses that a glycerine solution of zinc chloride or other acceptable zinc salts provides effective therapy for gingivitis when applied to the gingivae and teeth.

Efforts continue toward finding improved means for reducing and/or eliminating plaque without many of the side effects associated with the prior art, such as discoloration of teeth or tongue, desquamation and soreness of oral mucosa, objectionable taste, toxicity and imbalance of the oral flora. It is an object of the present invention to provide novel compositions which are useful in the treatment of plaque and gingivitis without many of the adverse side effects associated with prior art compositions. It is another object of this invention to provide anti-plaque compositions which would cause little or no ecological imbalance of the oral flora. It is a further object of this invention to provide compositions comprising a combination of a morpholinoamino alcohol and metal salts wherein these compositions possess synergistically improved anti-plaque and anti-gingivitis activity.

SUMMARY OF THE INVENTION

The present invention relates to novel compositions comprising a synergistic combination of a) a morpholinoamino alcohol or pharmaceutically-acceptable salt thereof and b) a metal salt. The morpholinoamino alcohol has the chemical formula.

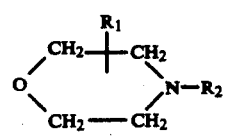

wherein $R_1$ is a straight or branched alkyl group containing 8 to 16 carbon atoms at the 2- or 3- position of the morpholino ring, and $R_2$ is a straight or branched alkyl group containing 2 to 10 carbon atoms terminating with a hydroxy group. The metal salt is selected from salts of the transition metals and the elements of Group 2A and Group 2B of the Periodic Table of the Elements. The preferred morpholinoamino alcohol is 3-(4-propylheptyl)-4-(2-hydroxyethyl) morpholine.

The compositions preferably comprise about 0.02–5% by weight of the morpholinoamino alcohol and about 0.0005–10% by weight of the metal salt. The compositions of this invention are useful in a wide variety of formulations, such as, for example, tooth paste, mouth wash, chewing gums and other dentifrices to reduce plaque or gingivitis. These compositions have synergistically improved anti-plaque and anti-gingivitis activity with less side effects. These compositions also possess synergistic antimicrobial and antiseptic activity.

DETAILED DISCUSSION

This invention involves novel compositions which have improved anti-plaque or anti-gingivitis activity. The novel compositions of the present invention comprise a synergistic combination of a pharmaceutically effective amount of a) one or more morpholinoamino alcohol(s) or pharmaceutically-acceptable salt(s) thereof and b) one or more metal salt(s).

The morpholinoamino alcohols useful according to this invention have the chemical formula

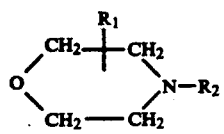

wherein $R_1$ is a straight or branched alkyl group containing 8 to 16 carbon atoms at the 2- or 3-position of the morpholino ring, and $R_2$ is a straight or branched alkyl group containing 2 to 10 carbon atoms terminating with hydroxy group. Preferably, the sum of the carbon atoms in said groups $R_1$ and $R_2$ ranges from 10 to 20, more preferably from 12 to 16. The morpholinoamino alcohols of this invention are described in U.S. Pat. No. 4,636,382; the disclosure of which is herein incorporated by reference.

The morpholinoamino alcohols can be prepared by several processes as described in U.S. Pat. No. 4,636,382, such as:

(a) by alkylating a morpholino derivative having the formula

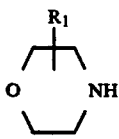

wherein $R_1$ is as defined above; with an alkylating agent of the formula $R_2X$ wherein $R_2$ is as defined above and X is halogen or an organic sulfonic ester, or wherein X together with a hydroxyl group present in $R_2$ is a reactive oxide;

(b) by ring closure of a compound having the general formula

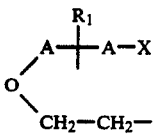

wherein $R_1$ is as defined above, X is halogen or an organic sulfonic ester and A represents $CH_2$ groups, one $CH_2$ group being substituted with the group $R_1$; with an amino alkanol of the general formula $NH_2R_2$ wherein $R_2$ is as defined above:

(c) by reducing a mono- or di-oxo substituted morpholine having the general formula

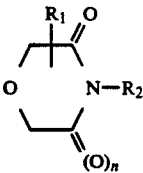

wherein $R_2$ is as defined above, n is 1 or 1, and $R_1$ is as defined above and is at the 2-position when n is 1 and at the 2- or 3-position when n is 0, or (d) by starting from a morpholino compound having the general formula

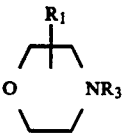

wherein $R_1$ is as defined above and $R_3$ is a straight or branched alkyl group containing a group transformable to OH or $CH_2OH$.

The most preferred morpholinoamino alcohol for use in this invention is 3-(4-propylheptyl)-4-(2-hydroxyethyl) morpholine represented by the chemical formula

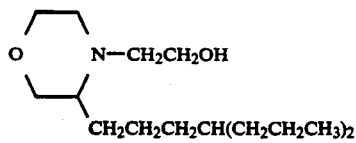

Also most preferred is the hydrochloride salt of 3-(4-propylheptyl)-4-(2-hydroxyethyl) morpholine. This compound is a white, odorless, crystalline powder which is very soluble in water, alcohols and chloroform and has a melting point of about 70° C.

The morpholinoamino alcohols of this invention can be used in their free base form or as pharmaceutically-acceptable salts thereof. Some examples of pharmaceutically-acceptable salts are the salts of acids such as acetic acid, phosphoric acid, boric acid, hydrochloric acid, maleic acid, benzoic acid, citric acid, malic acid, oxalic acid, tartaric acid, succinic acid, glutaric acid, gentisic acid, valeric acid, gallic acid, beta- resorcylic acid, acetyl salicylic acid, salicylic acid, perchloric acid, barbituric acid, sulfanilic acid, phytic acid, p-nitro benzoic acid, stearic acid, palmitic acid, oleic acid, myristic acid, lauric acid and the like. The most preferred salts are those of hydrochloric acid.

As the morpholinoamino alcohols of this invention by themselves have only weak anti-microbial activity, it is critical to the practice of this invention that said morpholinoamino alcohols be present in combination with one or more metal salts. It is the synergistic combination of said morpholinoamino alcohol and a metal salt which provides the compositions of this invention with their improved anti-plaque and anti-gingivitis properties. Without being bound by any theory or mechanism of action, it is believed that these morpholinoamino alcohols inhibit key bacterial membrane functions such as carbohydrate uptake, cellular permeability, cell metabolism and cell division. Bacterial cells which are weakened by these morpholinoamino alcohols are more effectively eradicated by the anti-microbial activity of the metal salts.

Compositions of this invention comprising a combination of said morpholinoamino alcohols and metal salts are extremely effective in inhibiting plaque formation and reducing preformed plaque and for treating gingivitis. These compositions have also demonstrated effectiveness in inhibiting acid production by bacteria such as Streptococcus mutans, and therefore these composition would have anti-caries activity.

Moreover, studies show a very low order of acute and subacute toxicity, no mutagenic activity, no adverse effect on reproduction and no staining of teeth by the morpholinoamino alcohols of the present invention.

Any of the metals known in the art to have anti-microbial properties may be used in the present invention. Suitable metals include the transition metals and the elements of Group 2A and Group 2B of the Periodic Table of the Elements. The transition metals include the elements 21-29 39-47, 57-79 and 89-103 of the Periodic Table. The preferred metal salts for use in this invention are the salts of divalent metal cations; most preferably the divalent metal cations of zinc, copper, calcium and magnesium. The metal cations are present as pharmaceutically-acceptable salts, such as chlorides, oxides, carbonates, hydroxides, citrates, acetates, lactates, salicylates and the like. The metal salts are utilized in the compositions of this invention in an amount ranging from about 0.0005% to about 10% by total weight of said composition; more preferably about 0.01% to about 5%; and most preferably from about 0.5% to about In the compositions of the present invention, the morpholinoamino alcohols are present preferably in an amount ranging from about 0.02% to about 5.0% by total weight of said composition; more preferably from about 0.02% to about 1.0%; and most preferably from about 0.02% to about 0.2%.

The essence of the present invention is the synergistic effect of inhibiting and reducing the growth of plaque bacteria, which is achieved when the morpholinoamino alcohols and the metal salts are utilized in combination in effective concentrations in the oral cavity. Smaller quantities of each of these components are required to obtain effective inhibition of plaque and other bacteria than if each component was utilized alone. Since lower quantities of each component can be used in the compositions of this invention, the side effects associated with each of the components would be correspondingly reduced or eliminated.

In one form of this invention, the composition may be a liquid such as a mouthwash or rinse. In such a composition the vehicle is typically a water-alcohol mixture. Generally the ratio of water to alcohol is in the range of from about 1:1 to about 20:1, preferably about 3:1 to about 20:1 and most preferably about 3:1 to about 10:1 by weight. The most preferred mouthwash or mouthrinse compositions comprise from about 0 to about 30% by weight alcohol, such as ethanol. The total amount of water-alcohol mixture in a mouthwash composition is typically in the range from about 70% to about 99.9% by weight of the composition. The pH value of such mouthwash compositions is generally from about 4.0 to about 7.0 and preferably from about 5 to about 6.5. A pH below 4 would be irritating to the oral cavity. A pH greater than 7 would result in an unpleasant mouth feel.

Oral liquid compositions may also contain surface active agents in amounts up to about 5% and fluorine-providing compounds in amounts up to about 2% by weight of the composition.

Surface active agents are organic materials which afford complete dispersion of the composition throughout the oral cavity. The organic surface active material may be anionic, non-ionic, amphoteric, or cationic. Suitable anionic surfactants are water-soluble salts of higher fatty acid monoglyceride monosulfates, such as the sodium salt of the monosulfated monoglyceride of hydrogenated coconut oil fatty acids; higher alkylsulfates, such as sodium lauryl sulfate; alkyl aryl sulfonates, such as sodium dodecyl benzene sulfonate; higher alkyl sulfonacetates; higher fatty acid esters of 1,2-dihydroxy propane sulfonates; and substantially saturated higher aliphatic acyl amides of lower aliphatic amino carboxylic acids such as those having 12 to 16 carbons at the fatty acid, alkyl or acyl radicals.

Non-ionic surface active agents include condensates of sorbitan mono-oleate with from 20 to 60 moles of ethylene oxide (e.g., "Tweens" a trademark of ICI United States, Inc.), condensates of ethylene oxide with propylene oxide and condensates of propylene glycol ("Pluronics" a trademark of BASF-Wyandotte Corp.).

Other suitable non-ionic surfactants are the condensation products of an alpha-olefin oxide containing 10 to 20 carbon atoms, a polyhydric alcohol containing 2 to 10 carbons and 2 to 6 hydroxyl groups and either ethylene oxide or a heteric mixture of ethylene oxide and propylene oxide. The resultant surfactants are heteric polymers having a molecular weight in the range of about 400 to about 1600 and containing 40% to 80% by weight of ethylene oxide, with a alpha-olefin oxide to polyhydric alcohol mole ratio in the range of about 1:1 to 1:3.

Amphoteric surfactants useful in the present invention are zwitterions having the capacity to act as either an acid or a base. They are generally non-irritating and non-staining. Non-limitative examples of suitable amphoteric surfactants include cocoamidopropyldimethylsultaine and cocodimethylbetaine (commercially available from Lonza Chem. Co. under the tradenames Lonzaine CS and Lonzaine 12C, respectively).

A fluorine providing compound may be present in the oral compositions of this invention. These compounds may be slightly water soluble or may be fully water soluble and are characterized by their ability to release fluroide ions or fluoride containing ions in water. Typical fluorine providing compounds are inorganic fluoride salts such as soluble alkali metal, alkaline earth metal, and heavy metal salts, for example, sodium fluoride, potassium fluoride, ammonium fluoride, cuprous fluoride, zinc fluoride, stannic fluoride, stannous fluoride, barium fluoride, sodium fluorosilicate, ammonium fluorosilicate, sodium fluorozirconate, sodium monofluorophosphate, aluminium mono-and difluorophosphate and fluorinated sodium calcium pyrophosphate.

In a oral liquid composition such as a mouthwash, the fluorine providing compound is generally present in an amount sufficient to release up to about 0.15%, preferably about 0.001% to about 0.05%, fluoride by weight of the composition.

The compositions of this invention may be substantially solid or pasty in character such as dental cream, toothpaste, toothpowder or chewing gum. Solid or pasty oral compositions contain polishing materials. Typical polishing materials are abrasive particulate materials having particle sizes of up to about 20 microns. Nonlimiting illustrative examples include: water-insoluble sodium metaphosphate, potassium metaphosphate, tricalcium phosphate, dihydrated calcium phosphate, anhydrous dicalcium phosphate, dicalcium phosphate, calcium pyrophosphate, magnesium orthophosphate, trimagnesium phosphate, calcium carbonate, alumina, aluminum silicate, zirconium silicates, silica, bentonite, and mixtures thereof. Polishing materials are generally present in an amount from about 20% to about 99% by weight of the composition. Preferably, it is present in amounts from about 20% to about 75% in toothpaste, and from about 70% to about 99% in toothpowder.

In clear gels, a polishing agent of colloidal silica and alkali metal aluminosilicate complexes are preferred since they have refractive indices close to the refractive indices of gelling agent liquid systems commonly used in dentifrices.

The compositions of the present invention may additionally contain sweeteners, flavorants and colorants.

In the instance where auxiliary sweeteners are utilized, the present invention contemplates the inclusion of those sweeteners well known in the art, including both natural and artificial sweeteners. Thus, additional sweeteners may be chosen from the following non-limiting list:

A. Water-soluble sweetening agents such as monosaccharides, disaccharides and polysaccharides such as xylose, ribose, glucose, mannose, galactose, fructose, dextrose, sucrose, maltose, partially hydrolyzed starch, or corn syrup solids and sugar alcohols such as sorbitol, xylitol, mannitol and mixtures thereof.

B. Water-soluble artificial sweeteners such as the soluble saccharin salts, i.e., sodium, or calcium saccharin salts, cyclamate salts, acesulfame-K and the like, and the free acid form of saccharin.

C. Dipeptide based sweeteners such as L-phenylalanine methyl ester and materials described in U.S. Pat. No. 3,492,131 and the like.

In general, the amount of sweetener will vary with the desired amount of sweetness selected for a particular composition. This amount will normally be 0.01% to about 40% by weight. The water-soluble sweeteners described in category A above, are preferably used in amounts of about 5% to about 40% by weight, and most preferably from about 10% to about 20% by weight of the final composition. In contrast, the artificial sweeteners described in categories B and C are used in amount of about 0.005% to about 5.0% and most preferably about 0.05% to about 2.5% by weight of the final composition. These amounts are ordinarily necessary to achieve a desired level of sweetness independent from the flavor level achieved from flavorants.

Suitable flavorings include both natural and artificial flavors, and mints such as peppermint, citrus flavors such as orange and lemon, artificial vanilla, cinnamon and various fruit flavors and the like. Both individual and mixed flavors are contemplated. The flavorings are generally utilized in amounts that will vary depending upon the individual flavor, and may, for example range in amounts of about 0.1% to about 6% by weight of the final composition.

The colorants useful in the present invention, include the pigments which may be incorporated in amounts of up to about 2% by weight of the composition. Also, the colorants may include other dyes suitable for food, drug and cosmetic applications, and known as F. D. & C. dyes and the like. The materials acceptable for the foregoing spectrum of use are preferably water-soluble. Illustrative examples include the indigo dye, known as F. D. & C. Blue No. 2, which is the disodium salt of 5,5-indigotindisulfonic acid. Similarly, the dye known as F.D. & C. Green No. 1, comprises a triphenylmethane dye and is the monosodium salt of 4-[4-N-ethyl-p-sulfobenzylamino) diphenylmethylene]-[ 1-(N-ethyl-N-p-sulfoniumbenzyl)-2,5-cyclohexadienimine]. A full recitation of all F.D. & C. and D. & C. colorants useful in the present invention and their corresponding chemical structures may be found in the Kirk-Othmer Encyclopedia of Chemical Technology, 3rd Edition, in Volume 6, at pages 561-595, which text is accordingly incorporated herein by reference.

The present invention also involves a method for treating teeth or gums to reduce plaque or gingivitis comprising applying to the surface of the teeth and/or gums the compositions of this invention as described earlier. The compositions can be applied to the teeth and gums by any conventional means such as brushing, spraying, painting or rinsing of the oral cavity and the like. The compositions not only retain plaque accumulation, but has been demonstrated to remove pre-existing plaque as well. Additionally, the compositions show a prolonged effect on plaque accumulation following cessation of treatment through about one week after use. The compositions of this invention also have synergistic anti-microbial and antiseptic activity and are also useful as a topical antiseptic or disinfectant which is applied externally to the skin.

The following examples are presented to further illustrate this invention. The examples are intended in an illustrative sense and not in a limitative sense. This invention includes the embodiments described herein and any equivalents thereof. All parts and percentages are on a weight basis unless otherwise indicated.

EXAMPLE I

A composition within the scope of this invention was prepared by mixing the ingredients presented in Table I below. This composition was useful as a mouthwash.

TABLE I

| Ingredient | Amount (% w/v) |
| --- | --- |
| 3-(4-propylheptyl)-4-(2-hydroxyethyl) morpholine hydrochloride | 0.05 |
| Zinc chloride | 0.05 |
| Sodium fluoride | 0.002 |
| Nonionic surfactant | 0.7 |
| Sorbitol solution (75% solids in water) | 50.0 |
| Ethanol (95% in water) | 10.0 |
| Coloring agent | 0.0004 |
| Flavoring agent | 0.15 |
| Deionized water | (quantity sufficient to 100%) |

TABLE I

| Ingredient | Amount (% w/v) |
| --- | --- |
| 3-(4-propylheptyl)-4-(2-hydroxyethyl) morpholine hydrochloride | 0.05 |
| Zinc chloride | 0.05 |
| Sodium fluoride | 0.002 |
| Nonionic surfactant | 0.7 |
| Sorbitol solution (75% solids in water) | 50.0 |
| Ethanol (95% in water) | 10.0 |
| Coloring agent | 0.0004 |
| Flavoring agent | 0.15 |
| Deionized water | (quantity sufficient to 100%) |

EXAMPLE II

A composition within the scope of this invention was prepared by mixing the ingredients presented in Table II below. This composition was useful as an oral spray.

TABLE II

| Ingredient | Amount (% w/v) |
| --- | --- |
| 3-(4-propylheptyl)-4-(2-hydroxyethyl) morpholine hydrochloride | 0.20 |
| Zinc chloride | 0.10 |
| Nonionic surfactant | 1.2 |
| Citric acid, hydrous | 0.07 |
| Ethanol (95% in water) | 12.0 |
| Glycerol | 20.0 |
| Sweetening agent | 0.01 |
| Flavoring agent | 0.10 |
| Deionized water | (quantity sufficient to 100%) |

EXAMPLE III

Compositions within the scope of this invention was prepared by mixing the ingredients presented in Table III below. These compositions were useful as a dentifrice.

TABLE III

| Ingredient | Amount (% w/v) |
|---|---|
| 3-(4-propylheptyl)-4-(2-hydroxyethyl) morpholine hydrochloride | 0.20 |
| Zinc chloride | 0.30 |
| Sodium fluoride | 0.24 |
| Hydrated silica | 10-50 |
| Xylitol | 10-40 |
| Xanthan gum | 0.1-1.5 |
| Cocobetaine | 0.1-1.5 |
| Flavoring agent | 0.9 |
| Deionized water | (quantity sufficient to 100%) |

EXAMPLE IV

A Composition within the scope of this invention was prepared by mixing the ingredients presented in Table IV below. This composition wase useful as an oral gel.

TABLE IV

| Ingredient | Amount (% w/v) |
|---|---|
| 3-(4-propylheptyl)-4-(2-hydroxyethyl) morpholine hydrochloride | 0.3 |
| Zinc chloride | 0.2 |
| Methyl cellulose | 2.0 |
| Sorbitol solution (70% solids in water) | 50.0 |
| Flavoring agent | 0.2 |
| Deionized water | (quantity sufficient to 100%) |

EXAMPLE V

Compositions within the scope of this invention (samples A and B) were prepared and tested against *Bacteroides melaninogenious*, a Gram-negative obligately anaerobic bacterium associated with human dental plaque. Comparative compositions (Samples C, D, E and F) were also prepared and tested against *Bacteroides melaninogenicus*. The results of these evaluations are presented in Table V below as the of the bacteria cells exhibiting cytoplasmic membrane destabilization and disruption after treatment with the respective compositions for 15 minutes at 37° C. The results show that divalent metal cations, such as magnesium and calcium, synergistically affect the destabilization/disruption of cell membranes when used in combination with 3-(4-propylheptyl)-4-(2-hydroxyethyl) morpholine hydrochloride. A functional cytoplasmic membrane is vital to the survival of a bacterium. Therefore, any agent or combination of agents which effectively destabilizes the cytoplasmic membrane will lead to bacteria cell death and a reduction in dental plaque.

TABLE V

| Sample (in water) | % Cells Exhibiting Membrane Disruption |
|---|---|
| A. [0.2% 3-(4-propylheptyl)-4-(2-hydroxyethyl) Morpholine hydrochloride and 0.00061% magnesium chloride] | 100 |
| B. [0.2% 3-(4-propylheptyl)-4-(2-hydroxyethyl) Morpholine hydrochloride and 0.072% calcium chloride] | 98.3 |
| C. [0.76% NaCl and 0.15% sodium phosphate buffer] | 2.8 |
| D. [0.2% 3-(4-propylheptyl)- | 90.3 |

TABLE V-continued

| Sample (in water) | % Cells Exhibiting Membrane Disruption |
|---|---|
| 4-(2-hydroxyethyl) Morpholine hydrochloride] | |
| E. [0.00061% magnesium chloride] | 5.5 |
| F. [0.072% calcium chloride] | 5.5 |

EXAMPLE VI

Compositions within the scope of this invention (samples G, H, I, and J) were prepared and tested against *Candida albicans* in vitro. Comparative compositions (Samples K, L, M, N, and O) were prepared and also tested. The results are presented in Table VI as the amount of cell growth after exposure times of 0.5, 1.0, 5.0 and 10.0 minutes, respectively. The results show that neither divalent metal (zinc oxide) nor 3-(4-propylheptyl)-4-(2-hydroxethyl) morpholine hydrochloride alone exhibited any anti-microbial activity against *Candida albicans*. However, the combination of the zinc oxide and the morpholinoamino alcohol HCL exhibited a complete cell kill within 30 seconds.

TABLE VI

| | CELL GROWTH Exposure Time (Minutes): | | | |
|---|---|---|---|---|
| Sample (in water) | 0.5 | 1.0 | 5.0 | 10.0 |
| G. [0.05% 3-(4-propylheptyl)-4-(2-hydroxyethyl) morpholine hydrochloride and 1% zinc oxide] | 0 | 0 | 0 | 0 |
| H. [0.05% 3-(4-propylheptyl)-4-(2-hydroxyethyl) morpholine hydrochloride and 10% zinc oxide] | 0 | 0 | 0 | 0 |
| I. [0.2% 3-(4-propylheptyl)-4-(2-hydroxyethyl) morpholine hydrochloride and 1% zinc oxide] | 0 | 0 | 0 | 0 |
| J. [0.2% 3-(4-propylheptyl)-4-(2-hydroxyethyl) morpholine hydrochloride and 10% zinc oxide] | 0 | 0 | 0 | 0 |
| K. [0.85% NaCl] | 2 | 2 | 2 | 2 |
| L. [0.05% 3-(4-propylheptyl)-4-(2-hydroxyethyl) morpholine hydrochloride] | 1 | 1 | 1 | 1 |
| M. [0.2% 3-(4-propylheptyl)-4-(2-hydroxyethyl) morpholine hydrochloride] | 1 | 1 | 1 | 1 |
| N. [1% zinc oxide] | 2 | 2 | 2 | 2 |
| O. [10% zinc oxide] | 2 | 2 | 2 | 2 |

Scale:
0 = no cell growth
1 = slight cell growth
2 = heavy cell growth

We claim:

1. An oral composition having synergistic activity in inhibiting the growth of plaque bacteria comprising in combination a synergistic pharmaceutically effective amount of a) a morpholinoamino alcohol or pharmaceutically-acceptable acid salt thereof, wherein said morpholinoamino alcohol has the chemical wherein $R_1$ is a straight or branched alkyl group containing 8 to 16 carbon atoms at the 2- or 3-position of the morpholino ring, and $R_2$ is a straight or branched alkyl group containing 2 to 10 carbon atoms terminating with a hydroxy group and b) a divalent metal cation, wherein said metal is selected from the group consisting of zinc, copper, magnesium, calcium, cobalt, nickel, iron, manganese, chromium, titanium, vanadium, scandium, yttrium, zirconium, niobium, molybdenum, technetium, ruthenium, rhodium, palladium, silver, cadmium, strontium, barium, tungsten, platinum, gold and mercury and salts thereof selected from the group consisting of chlorides, oxides, carbonates, hydroxides, citrates, acetates, lactates and salicylates.

2. The composition of claim 1 wherein said metal is selected from the group consisting of zinc, copper and magnesium.

3. The composition of claim 1 wherein the sum of the carbon atoms in said groups $R_1$ and $R_2$ is 10 to 20.

4. The composition of claim 1 wherein said morpholinoamino alcohol is 3-(4-propylheptyl)-4-(2-hydroxyethyl) morpholine.

5. The composition of claim 1 wherein the amount of said morpholinoamino alcohol ranges from about 0.02% to about 5.0% by weight of said composition.

6. The composition of claim 1 wherein the amount of said metal salt ranges from about 0.0005% to about 10% by weight of said composition.

7. The composition of claim 1 wherein said pharmaceutically-acceptable salts of the morpholinoamino alcohol are the salts of acids selected from the group consisting of acetic acid, phosphoric acid, boric acid, hydrochloric acid, malic acid, oxalic acid, tartaric acid, succinic acid, gallic acid, beta-resorcylic acid, acetyl salicylic acid, salicylic acid, perchloric acid, barbituric acid, sulfanilic acid, phytic acid p-nitro benzoic acid, stearic acid, palmitic acid, oleic acid, myristic acid and lauric acid.

8. The composition of claim 1 wherein said composition is a tooth paste.

9. The composition of claim 1 wherein said composition is a liquid mouthwash.

10. The composition of claim 1 wherein said composition is a chewing gum.

11. The composition of claim 9 wherein said mouthwash composition comprises from about 0 to about 30% by weight alcohol.

* * * * *